United States Patent
Vilei et al.

(10) Patent No.: US 8,173,162 B2
(45) Date of Patent: May 8, 2012

(54) PREPARATION FOR REPAIRING CARTILAGE TISSUE, ESPECIALLY ARTICULAR CARTILAGE DEFECTS

(75) Inventors: Simona Berardi Vilei, Lodrino (CH); Peter Bittmann, Zurich (CH); Philipp Wagner, Gland (CH); Martin Frenz, Muensingen (CH)

(73) Assignee: Zimmer Orthobiologics, Inc., Austin, TX (US)

( * ) Notice: Subject to any disclaimer, the term of this patent is extended or adjusted under 35 U.S.C. 154(b) by 135 days.

(21) Appl. No.: 10/547,437

(22) PCT Filed: Feb. 23, 2004

(86) PCT No.: PCT/CH2004/000093
§ 371 (c)(1),
(2), (4) Date: Jun. 16, 2006

(87) PCT Pub. No.: WO2004/075940
PCT Pub. Date: Sep. 10, 2004

(65) Prior Publication Data
US 2007/0148242 A1    Jun. 28, 2007

(30) Foreign Application Priority Data
Feb. 26, 2003   (CH) .................................. 0296/03

(51) Int. Cl.
*A61K 9/14* (2006.01)
(52) U.S. Cl. ........................................... 424/484
(58) Field of Classification Search .................. None
See application file for complete search history.

(56) References Cited

U.S. PATENT DOCUMENTS

| | | | |
|---|---|---|---|
| 4,394,370 A | 7/1983 | Jefferies | |
| 4,516,276 A | 5/1985 | Mittelmeier | |
| 4,624,672 A | 11/1986 | Lenkauskas | 623/10 |

(Continued)

FOREIGN PATENT DOCUMENTS

EP    1270025    *  1/2003

(Continued)

OTHER PUBLICATIONS

Hodges et al. (Journal of Biomedical Optics. Oct. 2001; 6(4): 427-431).*

(Continued)

*Primary Examiner* — Scott Long
(74) *Attorney, Agent, or Firm* — Schwegman, Lundberg & Woessner, P.A.

(57) ABSTRACT

The invention relates to preparations which are suitable for repairing enchondral or osteochondral defects (4) by means of implantation, said preparations comprising a cartilage element (A) and optionally a bone element (B) which is connected to the cartilage element (A). The cartilage element (A) can already contain cells during the implantation or is populated after the implantation with cells migrating from surrounding tissue. The aim of the invention is to better equip the cartilage element (A) of one such preparation for integration into the surrounding tissue and/or for an easy-to-achieve, primary stability. To this end, said cartilage element is not homogeneously embodied but has different characteristics in a peripheral and/or basal region (2, 3) to those in a central region (3). Said differing characteristics (A) relate to the structure and/or composition of the matrix used and/or to the cells established in the matrix, and are in no way used to prevent the migration of cells into the preparation from the surrounding tissue.

41 Claims, 2 Drawing Sheets

U.S. PATENT DOCUMENTS

| | | | |
|---|---|---|---|
| 4,627,853 A | 12/1986 | Campbell et al. | 623/16 |
| 5,007,934 A * | 4/1991 | Stone | 623/14.12 |
| 5,152,791 A | 10/1992 | Hakamatsuka et al. | 623/16 |
| 5,206,023 A | 4/1993 | Hunziker | 424/423 |
| 5,368,858 A | 11/1994 | Hunziker | 424/423 |
| 5,707,962 A | 1/1998 | Chen et al. | |
| 5,713,374 A | 2/1998 | Pachence et al. | 128/898 |
| 5,749,874 A | 5/1998 | Schwartz | 606/75 |
| 5,837,235 A | 11/1998 | Mueller et al. | 424/93.7 |
| 5,876,452 A * | 3/1999 | Athanasiou et al. | 623/23.72 |
| 5,902,741 A | 5/1999 | Purchio et al. | 435/240.23 |
| 6,017,348 A | 1/2000 | Hart et al. | 606/79 |
| 6,060,306 A | 5/2000 | Flatt et al. | 435/297.2 |
| 6,080,194 A | 6/2000 | Pachence et al. | 623/18 |
| 6,179,871 B1 | 1/2001 | Halpern | 623/11.11 |
| 6,235,316 B1 | 5/2001 | Adkisson | 424/548 |
| 6,251,143 B1 | 6/2001 | Schwartz et al. | 623/23.72 |
| 6,352,558 B1 | 3/2002 | Spector | 623/18.11 |
| 6,451,060 B2 | 9/2002 | Masuda et al. | 623/23.72 |
| 6,454,811 B1 | 9/2002 | Sherwood et al. | 623/23.76 |
| 6,623,963 B1 | 9/2003 | Muller et al. | |
| 6,662,805 B2 | 12/2003 | Frondoza et al. | |
| 6,852,125 B2 | 2/2005 | Simon et al. | 623/16.11 |
| 6,911,202 B2 | 6/2005 | Amir et al. | 424/93.7 |
| RE41,286 E | 4/2010 | Atkinson et al. | |
| 2001/0010023 A1 | 7/2001 | Schwartz et al. | 623/23.72 |
| 2001/0012965 A1 | 8/2001 | Masuda et al. | 623/11.11 |
| 2001/0039455 A1* | 11/2001 | Simon et al. | 623/23.51 |
| 2002/0072533 A1 | 6/2002 | Schrier et al. | 514/364 |
| 2002/0110544 A1 | 8/2002 | Goldberg et al. | 424/93.7 |
| 2003/0003127 A1 | 1/2003 | Brown et al. | 424/423 |
| 2003/0077821 A1 | 4/2003 | Sah et al. | 435/366 |
| 2003/0100947 A1 | 5/2003 | Nadler et al. | 623/11.11 |
| 2003/0134792 A1 | 7/2003 | Pike et al. | 514/12 |
| 2003/0211992 A1 | 11/2003 | Chen et al. | 514/12 |
| 2004/0039447 A1 | 2/2004 | Simon et al. | 623/13.11 |
| 2004/0076656 A1 | 4/2004 | Pavesio et al. | 424/423 |
| 2004/0097405 A1 | 5/2004 | Schrier et al. | 514/2 |
| 2004/0162622 A1 | 8/2004 | Simon et al. | 623/23.5 |
| 2004/0181232 A1 | 9/2004 | Re et al. | 606/86 |
| 2004/0219182 A1 | 11/2004 | Gomes et al. | |
| 2005/0226856 A1 | 10/2005 | Ahlfors | 424/93.7 |
| 2008/0269895 A1 | 10/2008 | Steinwachs et al. | |

FOREIGN PATENT DOCUMENTS

| | | |
|---|---|---|
| EP | 1 270 025 | 3/2003 |
| EP | 0 656 767 B1 | 2/2005 |
| EP | 1 112 348 B1 | 11/2005 |
| WO | WO93/15694 | 8/1993 |
| WO | WO95/33821 A1 | 12/1995 |
| WO | WO97/30662 A1 | 8/1997 |
| WO | WO-9746665 A1 | 12/1997 |
| WO | WO99/19005 | 4/1999 |
| WO | WO01/17463 | 3/2001 |
| WO | WO-0134166 A1 | 5/2001 |
| WO | WO02/10348 A2 | 2/2002 |
| WO | WO02/070030 | 9/2002 |
| WO | WO03/024463 A1 | 3/2003 |
| WO | WO-2007033509 A1 | 3/2007 |

OTHER PUBLICATIONS

Buckwalter et al. (Bone and Joint Healing. 2001; Chapter 8; pp. 1-16).*

Du et al. (Journal of Biomedical Materials. 50(4): 518-527).*

Züger et al., Lasers in Surgery and Medicine 28(5):427-434 (2001).

Atkinson et al., Journal of Cellular Biochemistry 65:325-339 (1997).

Benz et al., Biochemical and Biophysical Research Communications 293:284-292 (2002).

Trippel, The Journal of Rheumatology 22:129-132 (1995).

"U.S. Appl. No. 11/997,769, Advisory Action mailed Apr. 29, 2011", 3 pgs.

"U.S. Appl. No. 11/997,769, Final Office Action mailed Dec. 30, 2010", 6 pgs.

"U.S. Appl. No. 11/997,769, Non Final Office Action mailed Jul. 12, 2010", 11 pgs.

"U.S. Appl. No. 11/997,769, Preliminary Amendment filed Jun. 27, 2008", 3 pgs.

"U.S. Appl. No. 11/997,769, Response filed Mar. 30, 2011 to Final Office Action mailed Dec. 30, 2010", 9 pgs.

"U.S. Appl. No. 11/997,769, Response filed Apr. 21, 2010 to Restriction Requirement mailed Feb. 23, 2010", 9 pgs.

"U.S. Appl. No. 11/997,769, Response filed Jun. 24, 2011 to Advisory Action mailed Apr. 29, 2011", 9 pgs.

"U.S. Appl. No. 11/997,769, Response filed Oct. 12, 2010 to Non Final Office Action mailed Jul. 12, 2010", 11 pgs.

"U.S. Appl. No. 11/997,769, Restriction Requirement mailed Feb. 23, 2010", 6 pgs.

"Australian Application Serial No. 2006294351, First Examiner Report mailed Aug. 3, 2011", 1 pg.

"European Application Serial No. 05405547.0, European Search Report mailed Jun. 2, 2006", 6 pgs.

"European Application Serial No. 06775196.6, Office Action mailed Feb. 24, 2009", 4 pgs.

"European Application Serial No. 06775196.6, Response filed Aug. 13, 2009 to Office Action mailed Feb. 24, 2009", 10 pgs.

"International Application Serial No. PCT/CH2006/000503, International Search Report mailed Jan. 18, 2007", 2 pgs.

"International Application Serial No. PCT/CH2006/000503, Written Opinion mailed Jan. 18, 2007", 5 pgs.

Adkisson, H. Davis, et al., "The Potential of Human Allogeneic Juvenile Chondrocytes for Restoration of Articular Cartilage", The American Journal of Medicine vol. 38, (Apr. 27, 2010), 1324-1333.

Boden, S. D., et al., "In Vivo Evaluation of a Resorbable Osteoinductive Composite as a Graft Substitute for Lumbar Spinal Fusion", Journal of Spinal Disorders 10(1), (1997), 1-11.

Chen, A. C., et al., "Chondrocyte Transplantation to Articular Cartilage Explants In Vitro", Journal of Orthopaedic Research, 15, (1997), 791-802.

Damien, C. J., et al., "A Composite of Natural Coral, Collagen, Bone Protein and Basic Fibroblast Growth Factor Tested in a Rat Subcutaneous Model", Annales Chirugiae et Gynaecologiae Suppl, 207, (1993), 117-128.

Hollinger, Jeffrey O., et al., "Poly(alpha-hydroxy acids): carriers for bon morphogenetic proteins", Biomaterial, vol. 17, (1996), 187-194.

Kenley, R., et al., "Osseous regeneration in the rat calvarium using novel delivery systems for recombination human bone morphogenic protein-2 (rhBMP-2)", Journal of Biomedical Materials Research, vol. 28, (1994), 1139-1147.

Kurtis, M. S., et al., "Integrin-mediated Adhesion of Human Articular Chondrocytes to Cartilage", Arthritis & Rheumatism, 48(1), (2003), 110-118.

Schinagl, et al., "Effect of Sedding Duration on the Strength of Chondrocyte Adhesion to Articular Cartilage", Jounral of Orthopaedic Research, 17, (1999), 121-129.

* cited by examiner

PREPARATION FOR REPAIRING CARTILAGE TISSUE, ESPECIALLY ARTICULAR CARTILAGE DEFECTS

The invention is in the field of medical technology and concerns a preparation according to the preamble of the first independent claim. The preparation is used for repairing cartilage tissue, in particular, for repairing defects in articular cartilage.

A known method for repairing enchondral articular cartilage defects, i.e. articular cartilage defects which affect only the cartilage layer, but not the bone tissue beneath the cartilage layer, comprises introduction of cells having a chondrogenic potential (chondrocytes, stem cells, etc.) in suspension, in a gel, or in an advantageously resorbable matrix into the defect site. In order to reliably hold the introduced materials in the defect site immediately after the operation and during the healing phase, for example, a piece of periosteum is sutured over the defect site. Suitable matrix materials for the repairing enchondral defects are, for example, described in the publications U.S. Pat. No. 6,352,558 and WO-99/19005 (Geistlich). These matrix materials are multilayer membranes based on collagen and, before being introduced into the defect site, they are cut to the size of the defect site. These membranes comprise a matrix layer that consists, in particular, of collagen II and has a sponge-like structure suitable for being seeded with chondrocytes or other cells having a chondrogenic potential. Furthermore, the membranes comprise a barrier layer which, on implantation, is facing towards the subchondral bone plate. This barrier layer consists, in particular, of collagen I and III, and its structure, which is significantly denser than the structure of the matrix layer, is suitable for preventing migration of cells from the bone tissue into the repair site and also for preventing vascularization of the repair site. In order to retain the aforementioned membrane in the defect site, a piece of periosteum is sutured over it, in the way as mentioned above. It is also proposed to provide the membrane with a barrier layer on both sides, thus giving mechanical characteristics to the outer membrane side which permit the membrane to be sutured to the surrounding cartilage tissue.

Furthermore, it is known to repair osteochondral articular cartilage defects, i.e. defects which not only concern the articular cartilage tissue but also the bone tissue lying beneath the cartilage tissue, by implantation of advantageously resorbable preparations as, for example, described in publications WO 93/15694 and U.S. Pat. No. 5,152,791. These preparation comprise a cartilage part and a bone part, wherein the two parts differ from one another with regard to porosity and/or with regard to the material. The preparations are usually implanted in appropriately prepared openings (boreholes), wherein the opening has a somewhat smaller cross section than the preparation. The thus formed, so-called press-fit in the mechanically firmer bone tissue and the greater depth of the anchorage, in comparison to preparations positioned in enchondral defects, are usually sufficient to retain the implant in the defect site in such a way that it is able to remain in place even if the repaired joint is allowed to be loaded.

From the description above, it is clear that in accordance with the state of the art, it is necessary to either harvest periosteum or to use a correspondingly equipped matrix (e.g. with an outer barrier layer) in order to attain a sufficient, primary stability, which guarantees that the implant will remain in the defect site after implantation and during the healing phase. Therein the harvesting of periosteum is a relatively complicated operation and the corresponding equipment of the matrix may have a negative effect on other matrix functions.

Furthermore, it is evident that in addition to the problem of the primary stability of the implants, the problem regarding integration or in-growth of the implant, or of the repair tissue formed in its place during the healing phase, in the surrounding tissue needs to be solved also. It is found that implant integration in the cartilage tissue and in the subchondral bone plate (or in corresponding repair tissue) is not satisfactory in many cases.

The problem of the integration of an artificial cartilage replacement part in viable cartilage tissue is the same for an implant designed for repairing a meniscus, for example, for replacing a part of the inner edge region of the meniscus, wherein the implant is supposed to grow together with the cartilage tissue of the rest of the meniscus.

The object of the invention is to create a preparation for repairing defect sites in cartilage tissue, in particular for repairing articular cartilage, wherein the preparation according to the invention, in comparison to known preparations of the same purpose, is to be improved with regard to integration and/or primary stability and wherein the improvement is not to render the implantation operation more demanding. The invention refers to the repair of cartilage tissue, wherein the preparation in accordance with the invention is used to repair, for example, enchondral defects in joints or menisci and comprises only one part (cartilage part) which is to replace cartilage tissue, or wherein the preparation is used to repair osteochondral defects in joints and comprises in addition to the cartilage part a bone part for replacing bone tissue, which bone part is arranged adjacent to the cartilage part.

The objet is achieved by the preparation, as it is defined in the claims.

In contrast to corresponding preparations according to the state of the art, the cartilage part of the preparation in accordance with the invention is not homogeneous, but comprises a peripheral region (region adjacent to surrounding cartilage tissue after implantation) and/or a basal region (region adjacent to the subchondral bone plate after implantation or bordering the bone part of an implant), which peripheral and/or basal regions have characteristics which are suitable for enhancing integration and/or primary stability of the preparation and do not prevent cell migration, whereas the rest of the cartilage part, i.e. a central region does not have such characteristics, but is equipped for an optimal regeneration of cartilage tissue. It is found that using a cartilage part being best suited in different regions for different repair functions, it becomes possible to get improvements regarding integration and/or primary stability without impairment of the formation of functional repair tissue in the central region.

A matrix of the cartilage part of the preparation in accordance with the invention is at least partially resorbable and is based, for example, on collagen. The matrix may be seeded with cells having a chondrogenic potential and may possibly be cultured in vitro before implantation. The preparation may also be implanted without cells to be later populated by repair cells migrating into the matrix from the surrounding tissue. The above named characteristics of the peripheral and/or basal region of the cartilage part, which characteristics are different from the characteristics of the central region, belong to at least one of the following groups: characteristics of the matrix structure, characteristics of the matrix composition, and characteristics of the cells populating the matrix.

The invention is based, in particular, on the finding that for good integration of the repair tissue in surrounding tissue (cartilage and/or bone), it is advantageous, like in a healing wound, if little differentiated cells (for example, stem cells) are available in the integration region, in particular cells which are not highly differentiated but are rather more mobile and better capable of proliferation. On the other hand, for quick and successful regeneration of cartilage tissue in the central region, it is advantageous if highly differentiated cells are available, i.e. chondrocytes or cells which are, regarding there degree of differentiation, not greatly different from chondrocytes. Such cells are known not to be very mobile and not to be capable of much proliferation.

For attaining at the same time formation of good cartilage repair tissue and good integration of this cartilage repair tissue in the surrounding tissue, it is possible to use, instead of an appropriate selection of cells differing in regard to their degree of differentiation, or in addition to the latter, for example, the following measures:

for facilitating cell mobility and cell proliferation, the porosity of the matrix is selected to be greater in the peripheral and/or basal region than in the central region, wherein possibly additional measures regarding primary stability are needed.

for differentiating cells populating the matrix before implantation or cells which migrate into the matrix after implantation in a desired manner, the basal and/or peripheral region are equipped with factors in a way different from the central part.

The following detailed description of the invention refers to the following Figs., wherein.

Figure 1:
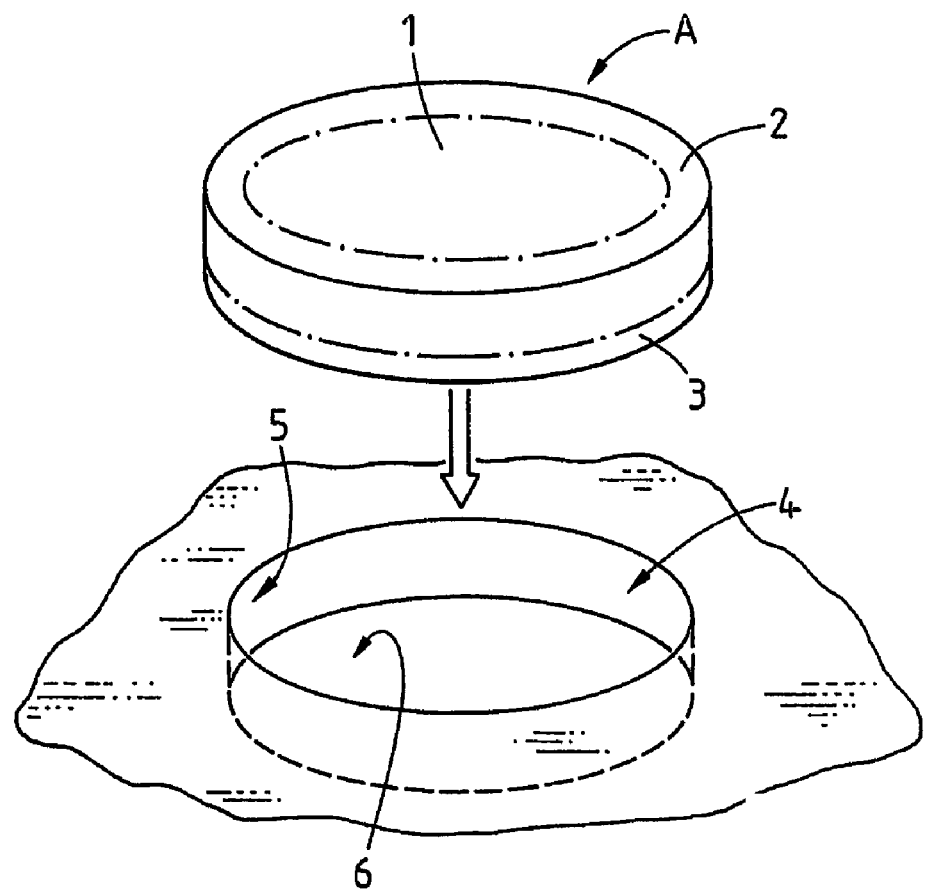
FIG. 1 shows an exemplary embodiment of the preparation in accordance with the invention, which embodiment is suitable for implantation in an enchondral defect site in articular cartilage, and the correspondingly prepared defect site.

FIG. 1 shows an exemplary embodiment of the preparation in accordance with the invention. The embodiment is suitable for repairing an enchondral defect in articular cartilage and comprises, for this reason, a cartilage part A only. The preparation, or the cartilage part respectively, has a central region 1, a peripheral region 2, and a basal region 3. The preparation is implanted with the basal region 3 facing towards the defect site 4, wherein the defect site may be suitably prepared before implantation. The defect site extends, through the cartilage layer 5, to the subchondral bone plate 6. In the implanted state, the basal region 3 of the preparation lies on the native subchondral bone plate 6.

The preparation has a thickness adapted to the thickness of the cartilage layer 5 to be repaired, i.e. a thickness of approximately 1-3 mm if used for repairing human articular cartilage. The flat expansion of the preparation is to be adapted to the defect site; the preparation has, for example, the form of a circular disk with a diameter of 3-10 mm. The peripheral region 2 and the basal region 3 of the preparation comprise, depending on the embodiment, a larger or a smaller part of the total volume of the preparation, but in most cases, the central region 1 assumes the largest part of the volume.

Especially in the case of preparations for the repair of enchondral defect sites in articulate cartilage, it is advantageous to design and/or to equip both the peripheral region 2 and the basal region 3 differently from the central region 1. However, it is also possible to do this for the peripheral region 2 only, so that the central region 1 extends over the entire thickness of the preparation, or for the basal region 3 only, so that the central region 1 extends over the entire flat expansion of the preparation.

Figure 2:
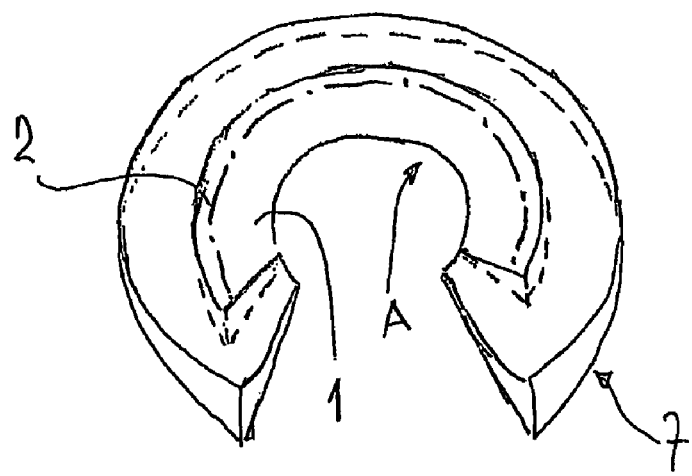
FIG. 2 shows a meniscus repaired with a preparation in accordance with the invention.

FIG. 2 shows a further exemplary embodiment of the preparation in accordance with the invention. This embodiment is suitable for replacing an inner edge region of a meniscus 7. The preparation, which comprises again a cartilage part A only is shown in the implanted position. Since the cartilage tissue of the meniscus 7 is not grown together with bone tissue, as is the case for articular cartilage, the preparation needs to be integrated only laterally in cartilage tissue of the meniscus, and for this reason, comprises only a central region 1 and a peripheral region 2, but no basal region.

Figure 3:
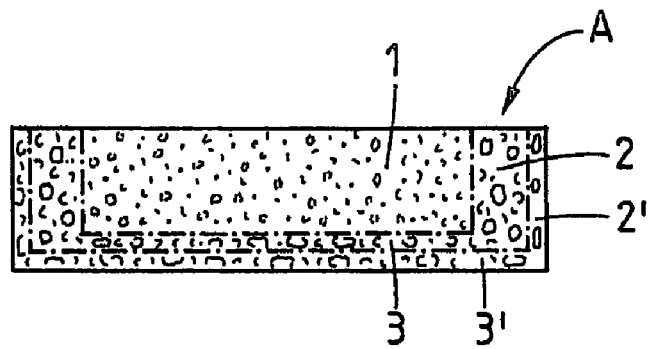
FIGS. 3 to 5 show sections through further exemplary embodiments of the preparation in accordance with the invention.
Figure 4:
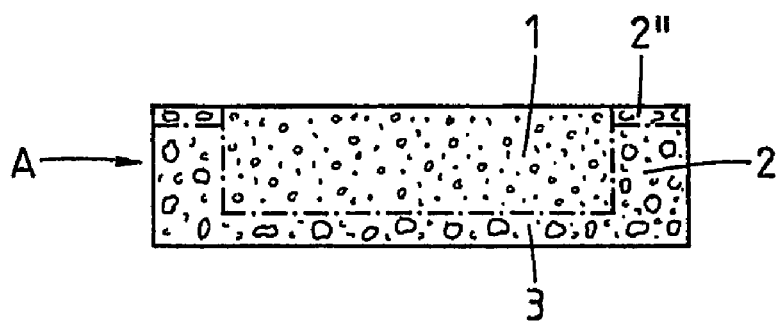

FIGS. 3 and 4 show in section two further exemplary embodiments of the preparation in accordance with the invention. The preparations according to FIGS. 2 and 3 essentially correspond to the preparation shown in FIG. 1, which is suitable for repairing an enchondral defect and comprises a cartilage part A only, but the peripheral region 2 and the basal region 3 (FIG. 3) or only the peripheral region 2 (FIG. 4) comprise additional subregions 2', 3', 2", which, in turn, have different characteristics in comparison to the rest of the peripheral or basal region. Advantageous such characteristics are described further below.

Figure 5:
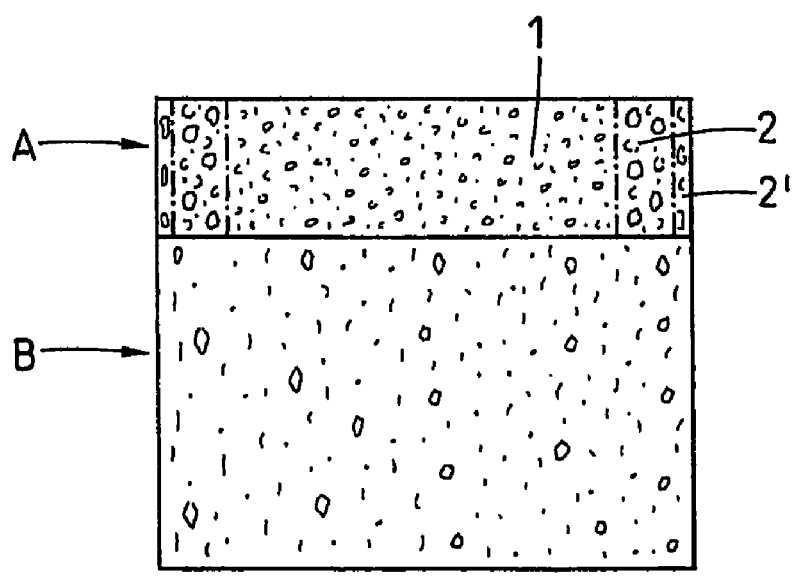

FIG. 5 shows a preparation suitable for repairing an osteochondral defect in a joint. For this reason, the preparation comprises not only a cartilage part A, but also a bone part B, attached to the cartilage part A. The cartilage part A is shaped, for example, as shown in FIG. 1, 3, or 4, or it has only a peripheral region 2 (possibly with a subregion 2') having characteristics different from the characteristics of the central region 1, which extends over the entire thickness of the cartilage element A.

The matrix of the preparation in accordance with the invention or of the cartilage part A of such a preparation respectively is suitable for being populated with cells, i.e. the matrix has an open porosity and consists of a correspondingly selected and/or correspondingly coated material. The matrix is at least partially biodegradable (resorbable). It consists in a per se known manner, for example, predominantly of collagen, collagen and calcium phosphate, or a resorbable polymer, for example, based on lactic acid and/or glycolic acid. The matrix may also be a natural product, i.e. it is, for example, produced from denatured cartilage tissue.

A matrix based on collagen is, for example, produced in a per se known manner, by cross-linking collagen fibers according to the DHT method (dehydrothermal cross-linking). A desired porosity is attained by a corresponding selection of method parameters. In particular, a higher porosity is produced if the collagen concentration is lower in the collagen base solution.

If the preparation in accordance with the invention comprises a bone part B in addition to the cartilage part A, the bone part is made in a per se known manner, for example, from a porous calcium phosphate, which enhances bone regeneration and is resorbed during the healing phase. The bone part may also consist of a resorbable plastic based on lactic acid and/or glycolic acid.

To produce a preparation in accordance with the invention, the preparation comprising a cartilage part with a matrix of collagen and a bone part with a matrix of porous calcium phosphate, the collagen is, for example, placed on the calcium phosphate substrate and is partially aspirated into it. Then, the collagen is cross-linked according to the DHT method.

Cells which are seeded in the central region 1, or which are to migrate into the central region, have the task, primarily, of replacing the implanted matrix with an intercellular matrix which is as cartilage-like as possible or to add such intercellular matrix to the implanted matrix. Chondrocytes, or cells with chondrogenic potential and in a stage of differentiation not far from that of chondrocytes, are particularly suitable for this task. It is found that in the peripheral and basal regions 2 and 3, where newly formed tissue is to be bonded to the existing tissue, the results are better when using, instead of chondrocytes, cells which have chondrogenic potential but which are in a less differentiated state than the cells of the central region. i.e., for example, pluripotent stem cells or mesenchymal stem cells. These less differentiated cells are also more mobile and better capable of proliferation than the aforementioned chondrocytes or chondrocyte-like cells. For a successful attachment of the repair tissue on the subchondral bone plate, cells which have osteogenic potential in addition to chondrogenic potential are likewise suitable.

Populating the various regions of the cartilage part A of the preparation in accordance with the invention with cells in various states of differentiation can, for example, be attained by using the same cells, for example, pluripotent or mesenchymal stem cells. Initially only the central region is seeded and the cells are then differentiated in vitro in the desired direction, by making corresponding factors promoting such differentiation available to the cells in the culture medium and/or in the matrix. Such a preliminary culturing normally requires a time period of 2-6 weeks. When the cells populating the central region have attained the desired degree of differentiation, the same cells as used for the initial seeding of the central region are then seeded in the peripheral and/or basal regions wherein it is advantageous to provide in these regions factors that promote cell proliferation, and possibly factors which promote cell differentiation to chondrocytes and which are made to be available in a delayed manner by e.g. being encapsulated.

A similar effect as achieved by preliminary culturing of the cells seeded in the central region as described above is attained by equipping the various regions of the matrix with various factors and by seeding all regions with the same cells (for example, stem cells) either immediately before implantation or with a short in vitro culture (for example, two-day) before implantation. Furthermore, the matrix may be implanted without cells, and the repair tissue is formed by cells which migrate into the matrix from surrounding tissue. In such a case, the central region is equipped with factors suitable for promoting the desired differentiation, wherein the factors are present in an immediately active form, and the peripheral and/or basal regions are equipped with factors suitable for promoting cell proliferation and present in an immediately active form. It is possible also to provide the peripheral and/or basal regions with factors promoting a desired differentiation and being equipped for delayed release.

Natural articular cartilage has more cells in outer layers than in inner layers bordering the subchondral bone plate. According to this model, it is advantageous to populate the basal region of the preparation in accordance with the invention with a smaller cell density than the central region, or possibly not to seed any cells therein. Cells migrating from the outermost region of the subchondral bone plate or from a boundary area between the cartilage tissue and the subchondral bone plate bordering the defect site will then migrate into the basal region, the cells having a state of differentiation suitable for this boundary area. In order to promote the cell migration into the basal region, the latter may be equipped with appropriate factors.

For only partial seeding the porous matrix with cells, for example, a suitable cell suspension is placed on the matrix surface and is aspirated into the matrix to the desired depth by applying a suction force from the opposite side of the matrix. For seeding a surface region with a small depth, it is possibly sufficient to apply the cell suspension on the corresponding matrix surface.

To equipping a matrix with factors, the factors are, for example, mixed with the matrix material and the mixture is then lyophilized. It is also possible to bind the factors with suitable linkers to the matrix or to add them, in dissolved or suspended form, to the finished matrix.

In order to not limit the capability of the cells regarding mobility and proliferation in the peripheral and/or basal regions by the matrix, it is advantageous to equip the matrix with a higher fraction of pores and/or with larger pores in the aforementioned regions than in the central region.

However, a highly porous matrix, especially a highly porous matrix in the peripheral region, is not suitable for suturing the matrix directly to the surrounding native cartilage tissue, because such a matrix has no sufficient tear resistance. For this reason other means for a good primary stability are advantageously provided. For example, a peripheral region or an outer subregion (FIGS. 3 and 5: 2') of the matrix is reinforced with fibers (for example, fibers of collagen II) or comprises a higher fraction of proteoglycans. Both these measures impart sufficient mechanical stability to the matrix regions for them to be able to be sutured without having to dispense with the high porosity, which according to the findings presented above is important, especially in this region.

It is also possible to attain suturing capability by reduction of the porosity, if this is done in an extremely small subregion, as is shown in the preparation in accordance with FIG. 4 (subregion 2"). In a matrix produced by lyophilization and consisting e.g. of collagen, a denser matrix structure in the peripheral region can be produced by pouring the collagen mass onto a cooling surface, wherein a very rapidly freezing and thus very finely structured and dense layer is formed directly on the cooling surface; this dense layer is then not completely removed as in accordance with the state of the art, but it is only removed where it would form the outer surface of the central preparation region. The denser layer is left in the peripheral region of this outer surface and forms a ring of a denser matrix material, which has a tear resistance sufficient for being capable to be reliable sutured to the surrounding cartilage material, even if the rest of the peripheral region does not have this tear resistance.

If the peripheral region of a preparation according to the invention has a mechanical stability which is not sufficient for suturing, it is also possible to integrate a bonding agent in the matrix in the peripheral and/or basal regions or in outer subregions thereof. Such bonding agent is activated in situ, for example, by means of lasers. A suitable such agent is, for example, an albumin adhesive, to which indocyanine green (for example, 0.1%), is admixed, and which is activated with a laser of a wavelength of 808 nm. A solution of the adhesive may be placed on peripheral and/or basal surfaces of the preparation, to then be fixed by lyophilization and to be activated by the laser after implantation. The preparation layer equipped with the adhesive advantageously has a thickness of no more than approx. 50 μm.

To promote integration of the preparation in the tissue surrounding the defect site, following the implantation, it is further advantageous to add to the peripheral and/or basal preparation regions inhibitors and/or antisense, which prevent or reduce degradation of the formed repair tissue and of the original tissue which directly borders thereon. Such advantageous additives are, for example, inflammation inhibitors, protease inhibitors, and/or apoptosis inhibitors.

The preparation in accordance with the invention is, for example, a preparation in accordance with FIG. 3, comprising a cartilage part of a matrix which has less porosity in the central region than in the peripheral and basal regions, whose central region is populated with cells which are in a state of higher differentiation (achieved by appropriate preliminary culturing) than cells in the peripheral and basal regions, and whose peripheral and basal surfaces (subregions 2' and 3') comprise an adhesive which can be activated with a laser. A similarly equipped preparation in accordance with FIG. 2, comprises in an analogous manner a central region of a smaller porosity than the peripheral region and being populated with further differentiated cells. Furthermore, an outer subregion of the peripheral region 2 is equipped with an adhesive.

A similar preparation which is to be populated only immediately before implantation with, for example, stem cells, or only after implantation with cells that migrate from the surroundings, has the same matrix, wherein the central region contains immediately acting factors suitable for promoting cell differentiation, and the peripheral and basal regions contain immediately acting factors promoting cell proliferation and delayed acting factors promoting cell differentiation.

In a preparation with a cartilage element and a bone element, only the peripheral region is equipped in the manner described above, and the basal region forms part of the central region (FIG. 5).

Depending on the quantity and type of cells available, depending on the type of use (enchondral or osteochondral defect sites in joints or meniscus defects, human or veterinary medicine, repair sites in loaded or less loaded joint areas, repair capacity of the native tissue around the repair site, etc.), fewer of the aforementioned measures are sufficient for a preparation to be integrated well in the surrounding tissue during the healing phase and to be implantable with simple means and with sufficient primary stability.

That is, in other words, a preparation in accordance with the invention can have, for example, at least in its cartilage part, a homogeneous matrix, and in the peripheral and/or basal regions thereof an adhesive activatable in situ and/or equipped with an inflammation-inhibiting agent. In such a case the peripheral and basal regions make up very little of the total volume of the cartilage part. On the other hand, the preparation in accordance with the invention may comprise nothing else of the inventive features than a matrix, whose structure in the central region is different from the structure in the peripheral region, especially less porous.

The invention claimed is:

1. An implant for a cartilage defect, comprising:
   an ex vivo prepared porous matrix populated with cells having chondrogenic potential;
   a peripheral region of the matrix having an outer surface for positioning adjacent native cartilage tissue surrounding the defect;
   a central region of the matrix having an outer surface adjacent an inner surface of the peripheral region;
   a basal region having an upper surface adjacent a lower surface of the peripheral region and a lower surface of the central region, the basal region having a lower surface for disposal on subchondral bone and between the subchondral bone and the lower surfaces of the peripheral and central regions; and
   wherein the peripheral region promotes proliferation of the cells having chondrogenic potential more than does the central region and the central region promotes differentiation of the cells having chondrogenic potential more than does the peripheral region.

2. The implant of claim 1, wherein the cells in the central region are closer to the state of differentiation of chondrocytes than cells in the peripheral and/or basal region.

3. The implant of claim 1, wherein the density of cells in the central region is greater than in the basal region.

4. The implant of claim 1, wherein the matrix is populated with cells in vitro.

5. The implant of claim 4, wherein the cells have chondrogenic potential.

6. The implant of claim 1, wherein the matrix includes a tissue degradation inhibitor in the peripheral and/or basal region.

7. The implant of claim 6, wherein the inhibitor includes an inflammation inhibitor, protease inhibitor, and/or apoptosis inhibitor.

8. The implant of claim 2, wherein the cells in the peripheral and/or basal region are stem cells.

9. The implant of claim 1, wherein the peripheral and/or basal region includes a bonding agent.

10. The implant of claim 9, wherein the bonding agent is activatable in situ.

11. The implant of claim 10, wherein the in situ activatable bonding agent comprises a mixture of an albumin adhesive with indocyanine green.

12. The implant of claim 1, wherein the matrix is suitable for repairing a defect in articular cartilage.

13. The implant of claim 1, wherein the matrix further comprises a bone part.

14. The implant of claim 4 wherein the cells in the central region are closer to the state of differentiation of chondrocytes than cells in the peripheral and/or basal region.

15. The implant of claim 4 wherein the density of cells in the central region is greater than in the basal region.

16. The implant of claim 4, wherein the cells in the basal region are of a different phenotypic potential than are the cells in the central and/or peripheral region.

17. The implant of claim 16, wherein the cells in the basal region have an osteogenic potential and the cells in the central and/or peripheral region have a chondrogenic potential.

18. The implant of claim 13, wherein the matrix is suitable for repairing an osteochondral defect.

19. The implant of claim 1, wherein the peripheral and/or basal region has a greater porosity and/or pores of greater size than the central region.

20. The implant of claim 1, wherein the matrix is populated with cells before implantation.

21. The implant of claim 13, wherein the bone part includes calcium phosphate.

22. The implant of claim 21, wherein the calcium phosphate is porous.

23. The implant of claim 1, wherein the matrix is at least partially biodegradable.

24. The implant of claim 23, wherein the matrix comprises a resorbable polymer.

25. The implant of claim 1, wherein the matrix comprises collagen.

26. The implant of claim 13, wherein the matrix comprises calcium phosphate.

27. The implant of claim 1, wherein the matrix is crosslinked.

28. The implant of claim 1, wherein the matrix is lyophilized.

29. The implant of claim 1, wherein the peripheral region includes a reinforcement.

30. The implant of claim 29, wherein the reinforcement comprises fibers.

31. The implant of claim 1, wherein the matrix has a thickness of about 1 mm to about 3 mm.

32. The implant of claim 1, wherein the matrix has a diameter of about 3 mm to about 10 mm.

33. The implant of claim 4, wherein the matrix is cultured in vitro prior to implantation.

34. The implant of claim 33, wherein the matrix is cultured for a time period of two days to six weeks.

35. The implant of claim 34, wherein the matrix is cultured for a time period of two weeks to six weeks.

36. The implant of claim 20, wherein the matrix is populated by applying a cell suspension.

37. The implant of claim 36, wherein the cell suspension is applied via aspiration.

38. The implant of claim 6, wherein the inhibitor is absent from the central region.

39. The implant of claim 1, wherein the volume of the central region is greater than the volume of the peripheral and/or basal region.

40. The implant of claim 9, wherein the bonding agent includes a tissue adhesive.

41. The implant of claim 9, wherein the bonding agent has a thickness of less than about 50 microns.

* * * * *